US 6,956,927 B2

(12) United States Patent
Sukeyasu et al.

(10) Patent No.: US 6,956,927 B2
(45) Date of Patent: Oct. 18, 2005

(54) RADIATION THERAPY PLANNING DEVICE

(75) Inventors: Katsunori Sukeyasu, Takatsuki (JP); Kazushige Tachibana, Ibaraki (JP)

(73) Assignee: Shimadzu Corporation, Nakagyo-Ku (JP)

( * ) Notice: Subject to any disclaimer, the term of this patent is extended or adjusted under 35 U.S.C. 154(b) by 0 days.

(21) Appl. No.: 10/836,142

(22) Filed: Apr. 29, 2004

(65) Prior Publication Data

US 2004/0228438 A1  Nov. 18, 2004

(30) Foreign Application Priority Data

May 16, 2003  (JP) .............................. 2003-138743

(51) Int. Cl.⁷ ................................................ A61N 5/10
(52) U.S. Cl. ........................... 378/65; 378/62; 378/901
(58) Field of Search ................... 378/65, 62, 4, 378/6, 64, 901, 208, 19, 98.8, 42

(56) References Cited

U.S. PATENT DOCUMENTS 5,132,996 A  *  7/1992  Moore et al. .................. 378/65
6,493,575 B1 * 12/2002 Kesten et al. ............... 600/431
6,768,784 B1 *  7/2004  Green et al. .................. 378/62

* cited by examiner

Primary Examiner—Edward J. Glick
Assistant Examiner—Irakli Kiknadze
(74) Attorney, Agent, or Firm—Darby & Darby (57) ABSTRACT

With regard to a radiation therapy planning device, the radiation planning fluoroscopic image shown on the screen of an image display monitor 6 is a large field fluoroscopic image P in which an in-progress fluoroscopic image PA is joined with a previously acquired fluoroscopic image PB. In addition, a large field fluoroscopic image P is acquired using an X-ray detector which does not produce any image distortions. As a result, the field of view for radiation planning fluoroscopic image is expanded by the amount of the previously acquired fluoroscopic image PB that is combined with the in-progress fluoroscopic image PA. In addition, with boundary line PL which is overlaid on the radiation planning fluoroscopic image, the boundary between fluoroscopic images PA and PB can be identified at a glance. As a result, even if in-progress fluoroscopic image PA and previously acquired fluoroscopic image PB is displayed simultaneously and contiguous to each other on the screen of the image display monitor 6, previously acquired fluoroscopic image PB does not interfere in the observation of the radiation planning fluoroscopic image. As a result, the field of view of the radiation planning fluoroscopic image in enlarged appropriately.

12 Claims, 7 Drawing Sheets

RADIATION THERAPY PLANNING DEVICE

INCORPORATION BY REFERENCE

The present application claims priority under 35 U.S.C. §119 to Japanese Patent Application No. 2003-138743 filed on May 16, 2003. The content of the application is incorporated herein by reference in its entirety.

TECHNICAL FIELD OF THE INVENTION

The present invention relates to a radiation therapy planning device which displays a radiation planning fluoroscopic image on an image display monitor. The radiation planning fluoroscopic image is used to design a plan for the radiation region in advance of radiation therapy of a subject who will be subjected to radiation therapy using a radiation irradiating device such as Linac to radiate a relevant area (malignant tumor and the like) within the body of the subject. In particular, the present invention relates to a technique for widening the field of view of the radiation planning fluoroscopic image that is shown on the image display monitor.

BACKGROUND OF THE INVENTION

In the prior art, radiation therapy is conducted by externally irradiating the relevant area (malignant tumor or the like) of a subject (patient) with radiation by using a radiation irradiating device called Linac (not shown) for example. With the radiation therapy, the area where the subject will be irradiated is planned in advance of the radiation therapy. In other words, the radiation area which is appropriate for the status (the condition of the diseased section) of the relevant region of the subject M is decided in advance. When the radiation is actually being carried out, only this radiation area is irradiated. In other words, if healthy area outside of the radiation area is irradiated, there will be damage to normal tissue, and conversely, if a part of the radiation area is not irradiated, the anticipated effect from radiation is not achieved. In order to have just enough radiation and not too much or too littler, there is a need to decide on the radiation area in advance.

For the planning of the radiation area, normally, as described below, a radiation therapy planning device that is separate from the radiation device is used. In other words, the design and planning of the radiation area is often conducted off line.

Figure 10:
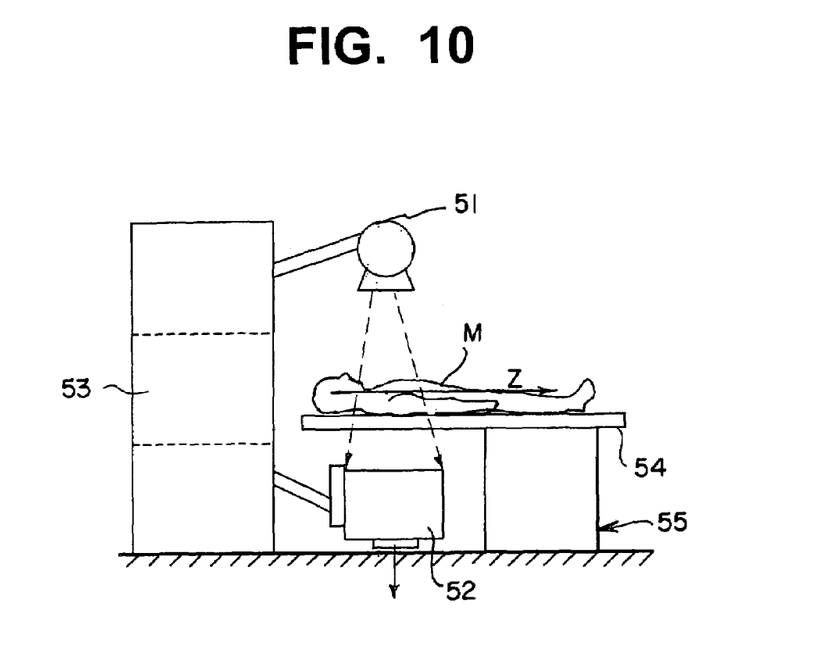
FIG. 10 is a schematic drawing showing the principal components of the radiation therapy planning device of the prior art.

In the radiation therapy planning device of the prior art, as shown in FIG. 10, a X ray tube 51, which shines a cone-shaped X ray beam at subject M, and an image intensifier (I—I tube) 52, which is a X ray detector detecting the fluoroscopic image from subject M, are placed on a gantry 53 opposite each other with subject M placed in between. A bed device 55 with a table 54 on which subject M is placed is in front of gantry 53. Table 54 can be moved vertically (raised and lowered), as well as horizontally in the lengthwise direction (forward and back; the Z direction of the body axis of subject M) and in the crosswise direction (side to side; perpendicular to the Z direction of the body axis of subject M). With the X ray irradiation of subject M by X ray tube 51, a fluoroscopic detection signal is outputted from I—I tube 52. Based on the fluoroscopic detection signal, a radiation planning fluoroscopic image is shown on the screen of an image display monitor (not shown) of a later stage. In addition, a film shooting mechanism (not shown) which is installed underneath table 54 conducts X ray film photography.

When planning the radiation area using the radiation therapy planning device, the planner observes the radiation planning fluoroscopy image on the screen of the image display monitor and decides the radiation area. When the planner has decided on a radiation area, X ray film shooting is conducted, and the radiation area is indicated by, for example, drawing a line showing the radiation area on the X ray film, and the planning for the therapy is completed.

The X ray film created by the radiation therapy planning device is sent to the operator of the radiation device. The operator of the radiation device will refer to the X ray film in which the radiation area is indicated and conduct treatment by external radiation of the relevant region (malignant tumor and the like) of subject M.

SUMMARY OF THE PRESENT INVENTION

However, with the radiation therapy planning device of the prior art in which fluoroscopy is conducted with I—I tube 52 as the X ray detector, the field of view of the radiation planning fluoroscopy image shown on the screen of the image display monitor is too narrow.

The screen of the image display monitor only displays the fluoroscopic image currently being photographed. Therefore, the area of the field of view of the radiation planning fluoroscopic image depends on the size of the X ray detection surface of I—I tube 52. However, because the size of the X ray detection surface of I—I 52 tube is not very large, the field of view of the radiation planning fluoroscopic image is also narrow. It would stand to reason that if the size of the X ray detection surface of I—I tube 52 is increased, the field of view of the radiation planning fluoroscopic image will become wider. However, in reality, even if the size of the X ray detection surface of I—I tube 52 is increased, there are large distortions in the image resulting from distortions in the image receiving surface of I—I tube 52 at the edges of the fluoroscopic image. Because the effective size of the X ray detection surface of I—I tube 52 does not increase, it is not possible to widen the field of view of the radiation planning fluoroscopic image shown on the screen of the image display monitor.

When the field of view of the radiation planning fluoroscopic image is narrow, in order to adequately observe the relevant region of subject M, the photographing position must be changed repeatedly by moving I—I tube 52 in a horizontal direction, and radiation planning fluoroscopic images with different fields of view are shown on the screen of the image display monitor. As a result, a long time is needed for the radiation planning process, and not only is the planning process inefficient, but this becomes cumbersome for subject M.

After considering the above situation, the object of the present invention is to provide a radiation therapy planning device that can appropriately widen the field of view of a radiation planning fluoroscopic image for designing a plan of the radiation area of a subject for radiation therapy.

In order to achieve this objective, the present invention has the following constitution.

According to a first implementation of the present invention, a radiation therapy planning device is equipped with an X ray tube for radiating X rays at a subject and an X ray detector which detects a fluoroscopic image. The subject is irradiated with X rays by the X ray tube, and based on the fluoroscopic detection signal outputted from the X ray detector, a radiation planning fluoroscopic image is shown on an image display monitor. The radiation planning fluoroscopic image is used to plan the radiation area of the radiation therapy subject in advance of the radiation therapy. For the X ray detector, a flat panel X ray detector is used. In addition, the radiation planning fluoroscopic image is a large field of view ("field") fluoroscopic image in which a portion or all of the fluoroscopic image that has already been acquired (previously acquired fluoroscopic image) and the fluoroscopic image currently being acquired (in-progress fluoroscopic image) are shown together. In areas where the in-progress fluoroscopic image overlaps with the previously acquired fluoroscopic image, the previously acquired fluoroscopic image is cut. A means for displaying a large field fluoroscopic image shows the large field fluoroscopic image together with a boundary indicator on the screen of an image display monitor. The boundary indicator shows the boundary between the in-progress fluoroscopic image and the previously acquired fluoroscopic image.

When planning the radiation area of a subject for radiation therapy in advance of radiation therapy using the radiation therapy planning device of the first implementation, the subject is irradiated with X rays by the X ray tube, and based on the fluoroscopic detection signal outputted from the flat panel X ray detector, a radiation planning fluoroscopic image is shown on the image display monitor. However, with the radiation therapy planning device of the first implementation, the radiation planning fluoroscopic image is a large field fluoroscopic image in which a portion or all of the fluoroscopic image that has already been acquired (previously acquired fluoroscopic image) is pasted onto the currently acquiring fluoroscopic image (in-progress fluoroscopic image), and in areas where the in-progress fluoroscopic image overlaps with the previously acquired fluoroscopic image, the previously acquired fluoroscopic image is cut. A means for displaying a large field fluoroscopic image shows the large field fluoroscopic image together with a boundary indicator on the screen of an image display monitor. The boundary indicator shows the boundary between the in-progress fluoroscopic image and the previously acquired fluoroscopic image. While observing the radiation planning fluoroscopic image shown on the screen of the image display monitor, the planner decides on the radiation area of the subject for radiation treatment.

According to the radiation therapy planning device of the first implementation, the radiation planning fluoroscopic image shown on the screen of the image display monitor is a large field fluoroscopic image in which a portion or all of the previously acquired fluoroscopic image is pasted onto the in-progress fluoroscopic image. In addition, with a flat panel X ray detector, there are no distortions in the image receiving surface, and there are no image distortions in the large field fluoroscopic image. As a result, the field of view of the radiation planning fluoroscopic image is widened by precisely the amount of a portion or all of the previously acquired fluoroscopic image that is pasted onto the in-progress fluoroscopic image. When the X ray detector is an image intensifier, the large field fluoroscopic image has image distortions resulting from the distortions in the image receiving surface of the I—I tube. As a result, even if the previously acquired fluoroscopic image is pasted onto the in-progress fluoroscopic image, the field of view of the radiation planning fluoroscopic image is not widened.

In addition, with the radiation planning fluoroscopic image, because of the accompanying boundary indicator, the area of the in-progress fluoroscopic image and the area of the previously acquired fluoroscopic image can be identified at a glance. As a result, even if the in-progress fluoroscopic image and the previously acquired fluoroscopic image is displayed simultaneously and adjacently on the screen of the image display monitor, the previously acquired fluoroscopic image does not interfere in the observation of the radiation planning fluoroscopic image.

Therefore, with the radiation therapy planning device of the first implementation, the radiation planning fluoroscopic image, which is for planning the radiation area of a subject for radiation therapy, has a wider field of view.

DETAILED DESCRIPTION OF THE PREFERRED EMBODIMENTS

Figure 1A:
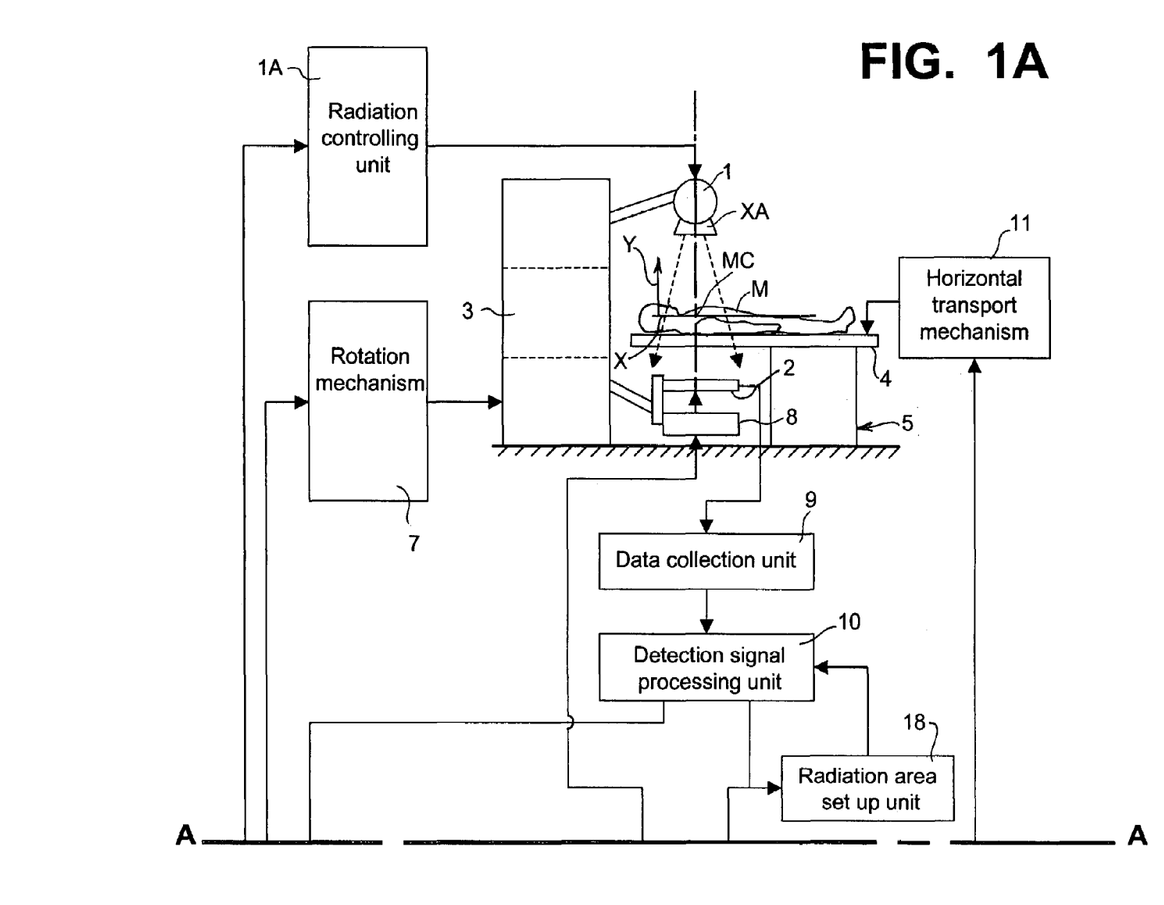
FIGS. 1A and 1B are a block diagram showing the entire constitution of a radiation therapy planning device of the present embodiment.
Figure 1B:
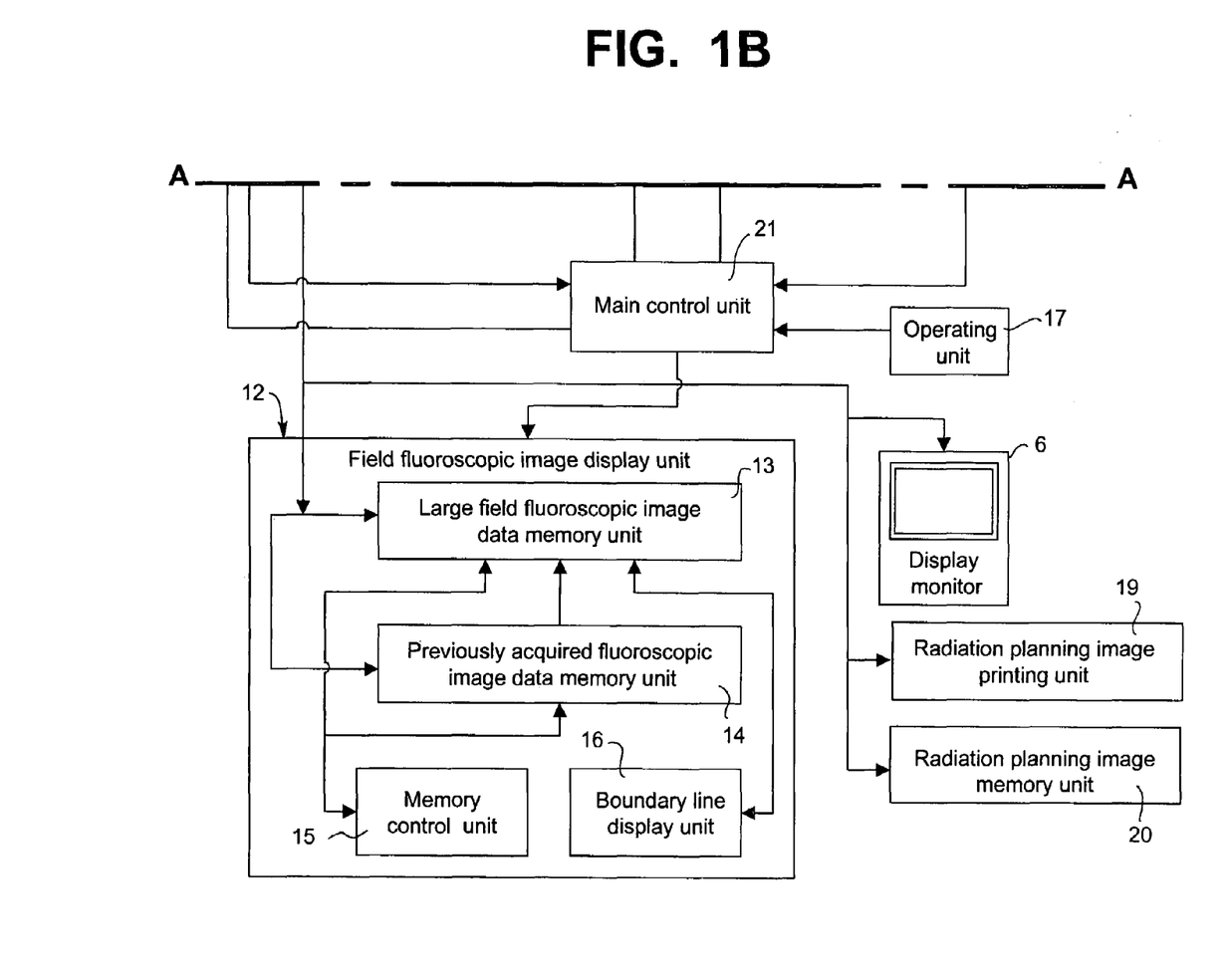

An embodiment of the present invention is described with reference to the figures. FIG. 1 is a block diagram showing the overall configuration of the radiation therapy planning device of the embodiment.

In the radiation therapy planning device of the embodiment as shown in FIG. 1, a X ray tube 1, which shines a cone-shaped X ray beam at a subject M, and a flat panel X ray detector (FPD) 2 as a X ray detector for detecting a fluoroscopic image from subject M are placed opposite of each other on a gantry 3 with subject M placed in between. A bed device 5 is in front of gantry 3 and has a table 4 on which subject M is placed. Table 4 can be moved horizontally in the lengthwise direction (forward and back; the Z direction of the body axis of subject M) and in the crosswise direction (side to side; in the X direction which is perpendicular to the Z direction of the body axis of subject M). As will be described in detail later, with X ray radiation of subject M by X ray tube 1, a fluoroscopic detection signal is outputted from FPD2. Based on this detection signal, a radiation planning fluoroscopic image is shown on an image display monitor 6 of a later stage. This radiation planning fluoroscopic image is for planning the radiation area of the subject M in advance of radiation therapy.

X ray tube 1 and FPD2 are placed opposite each other so that, at the standard position, a X ray axis XA connecting the focal point of X ray tube 1 and the center of the X ray detection surface passes through the isocenter (mechanical center) MC of the device. In addition, X ray tube 1 and FPD2 can be rotated by a rotation mechanism 7 while maintaining their opposing placement. The rotation axis is a horizontal axis that passes through isocenter MC. In other words, by rotating X ray tube 1 and FPD2 by rotation mechanism 7 around a horizontal axis, the camera angle (photographing direction) can be changed by changing the direction of irradiation of the X ray beam by X ray tube 1.

X ray tube 1 is controlled by radiation controlling unit 1A which includes a high voltage power source (not shown) and irradiates subject M on table 4 with a cone-shaped X ray beam.

FPD2 is a flat-shaped, light-weight detector in which an extremely large number of X ray detection elements of semiconductor elements or the like are arrayed on a X ray detection surface as a matrix of around 1024×1024 for example. FPD2 does not have any distortions in its image receiving surface, and as a result, FPD2 is a X ray detector without the distortions at the edges of the image caused by distortions in the image receiving surface as seen in image intensifiers.

In addition, FPD2 can be moved back and forth in the direction of X ray axis XA and in the direction of the surface of the X ray detection surface by a panel transport mechanism 8. In other words, by moving FPD2 in the direction of X ray axis XA, the fluoroscopic image at the X ray detection surface can have different enlargements. In addition, by moving FPD2 in the surface direction of the X ray detection surface, the camera position can be changed.

With the irradiation of subject M with X rays by X ray tube 1, a fluoroscopic detection signal is outputted from FPD2 and is collected by a data collection unit (DAS) 9 and is sent to a detection signal processing unit 10 of a later stage. Detection signal processing unit 10 processes the fluoroscopic detection signal into a fluoroscopic image and this is sent to image display monitor 6. The fluoroscopic image sent to image display monitor 6 is shown on a screen as a radiation planning fluoroscopic image.

Table 4 can be moved in the table lengthwise direction (in the Z direction of the body axis of subject M) and in the table crosswise direction (in the X direction which is perpendicular to the Z direction of the body axis of subject M) by a horizontal transport mechanism 11. In other words, by moving table 4 lengthwise or crosswise, the position of subject M which faces X ray tube 1 is changed, thereby changing the camera position. Table 4 can also be raised and lowered (Y direction) by the horizontal moving mechanism (not shown). When subject M is going on or getting off table 4, table 4 is lowered.

Figure 2:
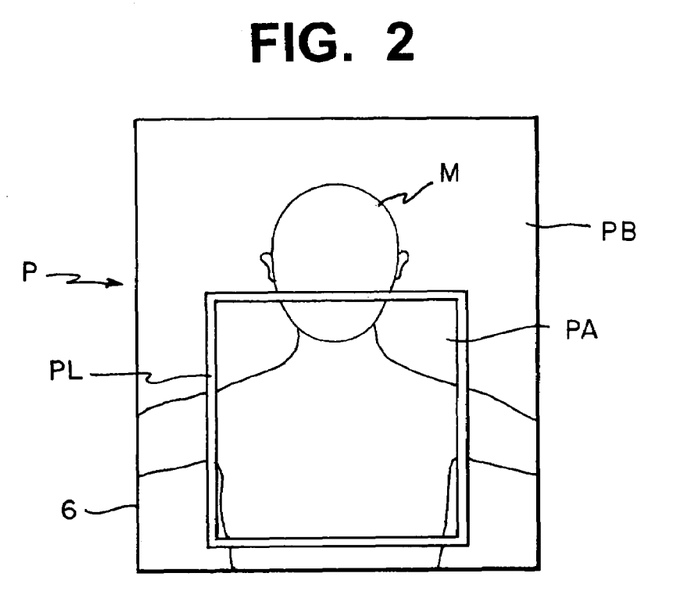
FIG. 2 is a cartoon showing one example of a large field fluoroscopic image displayed by the present embodiment.

Furthermore, with the radiation therapy planning device of the present embodiment, in order to have a wider field of view of a radiation planning fluoroscopic image, the radiation planning fluoroscopic image is a large field fluoroscopic image P. In large field fluoroscopic image P, a portion or all of the fluoroscopic image that has already been acquired (previously acquired fluoroscopic image) PB is pasted onto the currently acquiring fluoroscopic image (in-progress fluoroscopic image) PA, and in areas where in-progress fluoroscopic image PA overlaps with previously acquired fluoroscopic image PB, previously acquired fluoroscopic image PB is cut. A large field fluoroscopic image display unit 12 shows large field fluoroscopic image P together with a boundary indicator on the screen of an image display monitor 6. The boundary indicator shows the boundary between the fluoroscopic images PA, PB. Stated more concretely, in the device of the present embodiment, as shown in FIG. 2 for example, by using large field fluoroscopic image display unit 12, large field fluoroscopic image P, in which in-progress fluoroscopic image PA is pasted onto previously acquired fluoroscopic image PB, is shown on the screen of image display monitor 6 together with boundary line PL which is a boundary indicator showing the boundary between in-progress fluoroscopic image PA and previously acquired fluoroscopic image PB. We will describe in further detail the construction of large field fluoroscopic display unit 12.

With the device of the present embodiment, as shown in FIG. 1, large field fluoroscopic image display unit 12 comprises a large field fluoroscopic image data memory unit 13 and previously acquired fluoroscopic image data memory unit 14 and a memory control unit 15 and a boundary line display unit 16. Memory control unit 15 controls the memory operations of both memory units 13, 14.

Large field fluoroscopic image data memory unit 13 stores image data of a single large field fluoroscopic image P. In other words, large field fluoroscopic image data memory unit 13 stores image data of both the in-progress fluoroscopic image PA, which is being sent from detection signal processing unit 10 in real time, and the necessary portion of previously acquired fluoroscopic image PB which is to be pasted. With large field fluoroscopic image data memory unit 13, each time new image data of in-progress fluoroscopic image PA is received from detection signal processing unit 10, updating of data takes place. Large field image P which is stored in large field image data memory unit 13 is read by memory control unit 15 at appropriate times and outputted to image display monitor 6.

Previously acquired fluoroscopic image data memory unit 14 stores image data for previously acquired fluoroscopic image PB, which is to be pasted to in-progress fluoroscopic image PA, together with acquiring position data. With the device of the present embodiment, the acquiring position data of previously acquired fluoroscopic image PB is the position data of table 4 in the table lengthwise direction and position data in the table crosswise direction sent from horizontal transport mechanism 11 of table 4, position data in the X ray axis XA direction of FPD2 and position data in the surface direction of X ray detection surface of FPD2 sent from panel transport mechanism 8, and the like.

In addition, with the device of the present embodiment, previously acquired fluoroscopic image PB stored in previously acquired fluoroscopic image data memory unit 14 can be designated on the screen of image display monitor 6 by the planner as to what is thought to be appropriate using an operating unit 17 which comprises input devices of mouse or keyboard or the like. There is no limit on the number of stored images of previously acquired fluoroscopic image PB. All of previously acquired fluoroscopic PB image assigned by operating unit 17 is stored in the memory as long as it does not exceed the memory. However, previously acquired fluoroscopic image PB with the same position data are not stored in duplicate.

Figure 3:
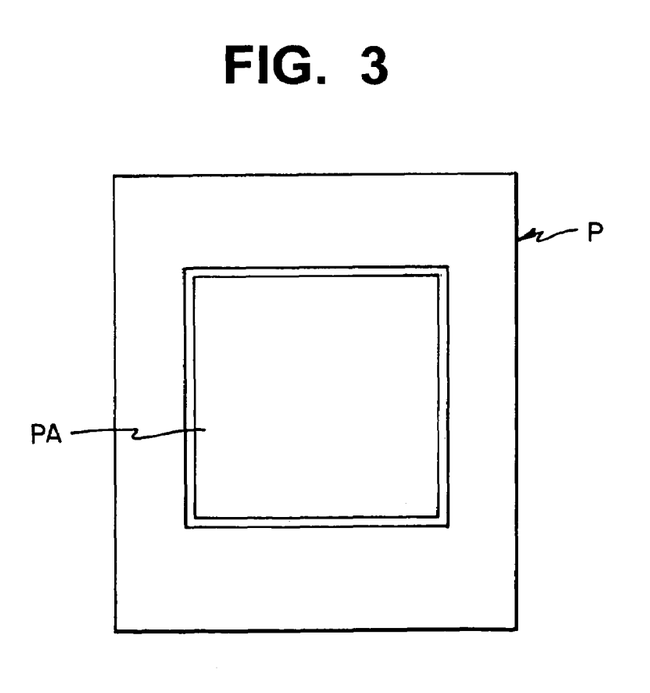
FIG. 3 is a cartoon for explaining the position of an in-progress fluoroscopic image within the large field fluoroscopic image.

Referring to FIG. 3, with regard to in-progress fluoroscopic image PA, image data of in-progress fluoroscopic image PA is stored in large field fluoroscopic image data memory unit 13 so that at the standard position where the center of FPD2 coincides with X ray axis XA, the center of in-progress fluoroscopic image PA coincides with the center of large field fluoroscopic image P. In addition, as FPD2 moves further away from X ray axis XA along the plane of the X ray detection surface, the position of in-progress fluoroscopic image PA within large field fluoroscopic image P also changes in accordance with the direction and distance of movement.

Figure 4:
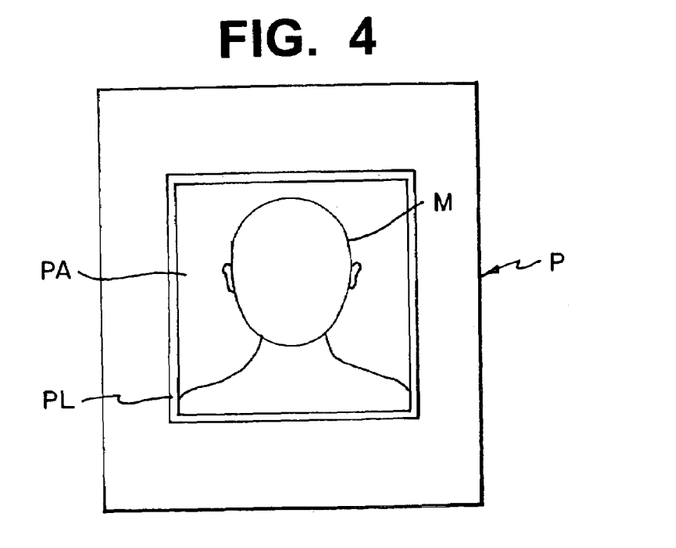
FIG. 4 is a cartoon showing an example of a display image of the in-progress fluoroscopic image within the large field fluoroscopic image.
Figure 5:
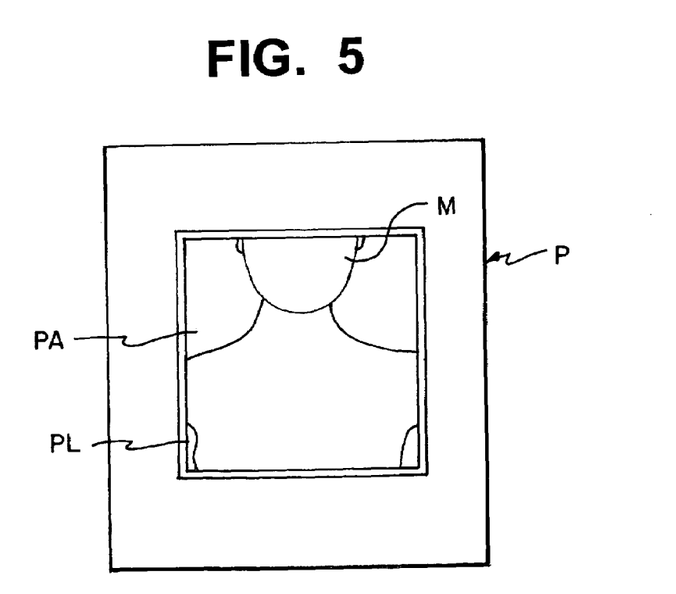
FIG. 5 is a cartoon showing an example of a change in the display image of the in-progress fluoroscopic image within the large field fluoroscopic image resulting from a change in the position of the FPD.

Therefore, when FPD2 is at the standard position where its center coincides with X ray axis XA, if the camera position is changed only by the horizontal movement of table 4, the position of in-progress fluoroscopic image PA within large field fluoroscopic image P does not change, and only the display content of in-progress fluoroscopic image PA changes. For example, when table 4 is moved in the table lengthwise direction, large field fluoroscopic image P changes from the image shown in FIG. 4 to the image shown in FIG. 5 in which there is a different display content for in-progress fluoroscopic image PA.

Figure 6:
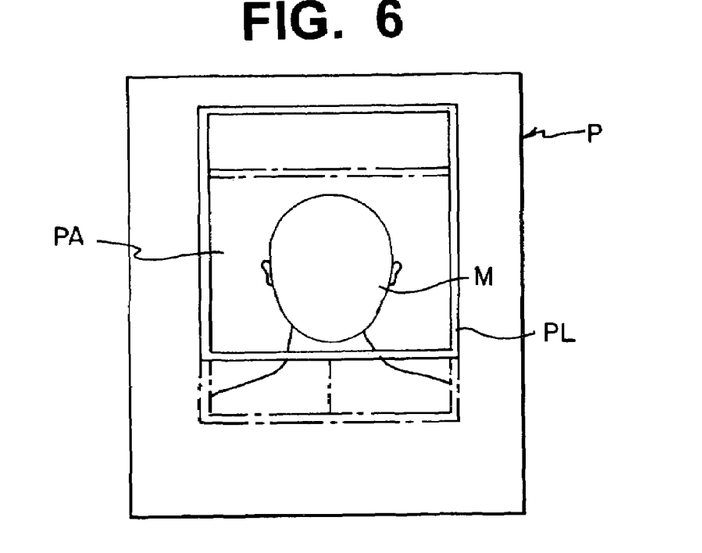
FIG. 6 is a cartoon showing an example of a change in the display image of the in-progress fluoroscopic image within the large field fluoroscopic image resulting from a change in the position of the FPD.
Figure 7:
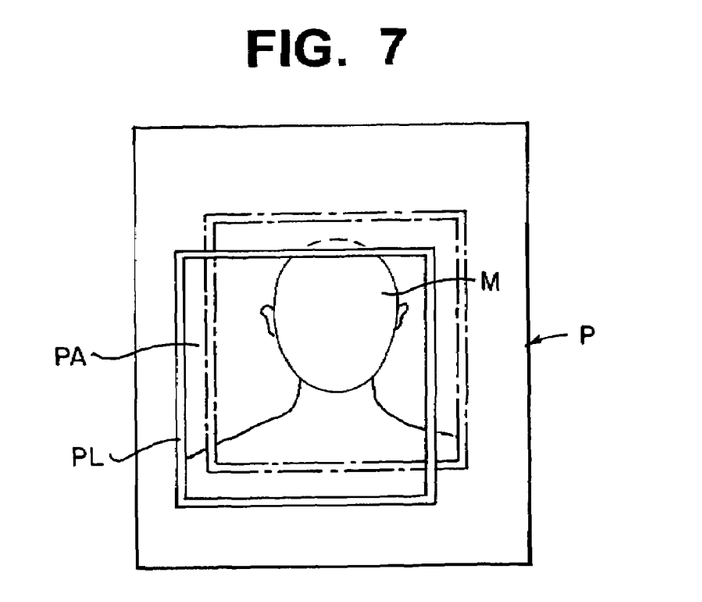
FIG. 7 is a cartoon showing another example of a change in the display image of the in-progress fluoroscopic image within the large field fluoroscopic image resulting from a change in the position of the FPD.

Furthermore, while keeping table 4 in the same position, if the camera position is changed by moving FPD2 along the plane of the X ray detection surface, both the position of in-progress fluoroscopic image PA within large field fluoroscopic image P and the display content of in-progress fluoroscopic image PA are changed. As shown in FIG. 6, when FPD2 is moved towards the head in the Z direction of the body axis of subject M, the position of in-progress fluoroscopic image PA within large field fluoroscopic image P moves upward, and the display content of in-progress fluoroscopic image PA also changes to an image towards the head of subject M. Referring to FIG. 7, if FPD2 is moved diagonally towards the feet of subject M along the Z direction of the body axis of subject M and along the X direction which is perpendicular to the body axis Z direction, the position of in-progress fluoroscopic image PA within large field fluoroscopic image P also shifts diagonally downward. At the same time, the display content of in-progress fluoroscopic image PA also changes to an image diagonally towards the feet.

With regard to previously acquired fluoroscopic image PB, based on the position data that is stored together with previously acquired fluoroscopic image PB and the size data of in-progress fluoroscopic image PA and previously acquired fluoroscopic image PB, data for the pixels surrounding in-progress fluoroscopic image PA in image data memory unit 13 are extracted so that in the areas where previously acquired fluoroscopic image PB overlaps with in-progress fluoroscopic image PA, the data for previously acquired fluoroscopic image PB is cut. This is stored in large field image data memory unit 13. As a result, in-progress fluoroscopic image PA and previously acquired fluoroscopic image PB are joined together successfully. When in-progress fluoroscopic image PA is updated, if there is no change in the camera position of in-progress fluoroscopic image PA before and after the update, the field of view is the same. Therefore, the image data of previously acquired fluoroscopic image PB does not need to be updated and is kept the same.

In addition, there may be differences in the image magnification between previously acquired fluoroscopic image PB and in-progress fluoroscopic image PA as a result of enlargement of the fluoroscopic image at the X ray detection surface of FPD2. Based on the position data of FPD2 in the X ray axis XA direction received from panel transport mechanism 8, the image magnification of previously acquired fluoroscopic image PB is adjusted to coincide with that of in-progress fluoroscopic image PA, and the image data is stored in large field image data memory unit 13.

The data storage operations for both data memory unit 13 and data memory unit 14 described above are closely controlled by memory control unit 15.

Furthermore, with regard to the present embodiment, in large field fluoroscopic image data memory unit 13, the image pixels at the perimeter of in-progress fluoroscopic image PA are programmed and stored to be 100% white level (or 100% black level) by boundary line display unit 16. In other words, because the pixels at the perimeter of in-progress fluoroscopic image PA are stored as 100% white (or 100% black) by boundary line display unit 16, the pixels at the edge of in-progress fluoroscopic image PA are 100% white (or 100% black), and this appears in large field fluoroscopic image P as a boundary line PL which clearly indicates the boundary with previously acquired fluoroscopic image PB.

In addition, with the present embodiment, when setup for enlarged fluoroscopic mode is selected by using operating unit 17, large field fluoroscopic image display unit 12 is activated. When not set up for enlarged fluoroscopic mode, large field fluoroscopic image display unit 12 is not activated, and in-progress fluoroscopic image PA is sent directly from detection signal processing unit 10 to image display monitor 6. Only in-progress fluoroscopic image PA is displayed as the radiation planning fluoroscopic image on the screen of image display monitor 6.

With the present embodiment, as described above, previously acquired fluoroscopic image PB to be stored in previously acquired fluoroscopic image data memory unit 14 is designated by the planner using operation unit 17. However, as described below, previously acquired fluoroscopic image PB stored in previously acquired fluoroscopic image data memory unit 14 can be automatically selected and stored based on the camera position data.

For example, the camera position can be successively checked, and previously acquired fluoroscopic image PB with camera positions that have not yet been stored are all selected and stored together with their camera position data. In this situation, there are no particular limitations on the number of images stored for previously acquired fluoroscopic image PB. When there is not enough memory for previously acquired fluoroscopic image PB which has been selected by operating unit 17, old stored data can be erased automatically and new data for previously acquired fluoroscopic image PB can be stored. However, previously acquired fluoroscopic image PB with the same position data are determined to be already stored and not stored again.

In large field fluoroscopic image data memory unit 13, when updating the image data for in-progress fluoroscopic image PA, if there are changes in the camera position of in-progress fluoroscopic image PA, the image data for the area surrounding in-progress fluoroscopic image PA in large field fluoroscopic image P is extracted and edited from previously acquired fluoroscopic image PB according to the camera position data for in-progress fluoroscopic image PA and camera position data for previously acquired fluoroscopic image PB. This is stored in large field fluoroscopic image data memory unit 13, and large field fluoroscopic image P is completed and outputted.

Figure 8:
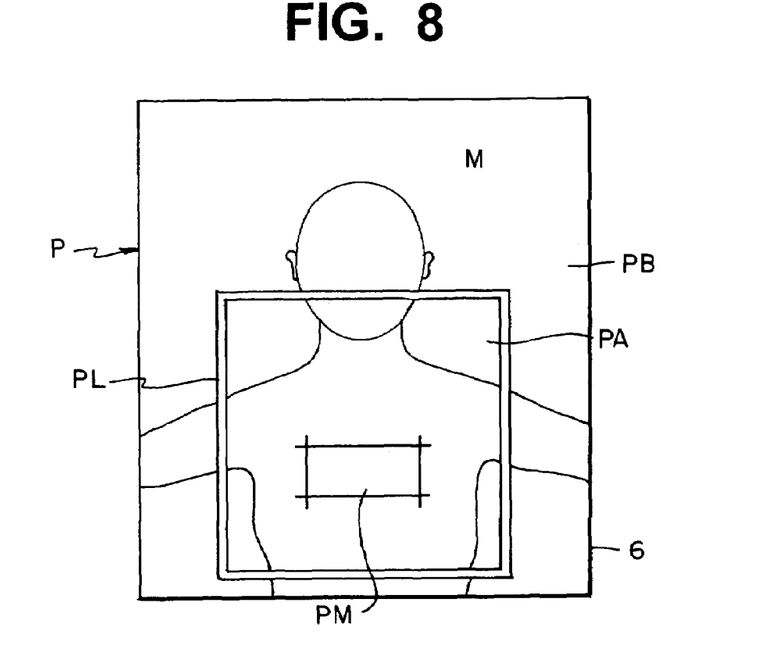
FIG. 8 is a cartoon showing an example of a radiation planning fluoroscopic image in which a radiation region PM is overlaid.

Furthermore, with the present embodiment, the planner establishes the radiation area on the screen of image display monitor 6 by using operation unit 17. Referring to FIG. 8, radiation area PM which has been established by radiation area setup unit 18 is displayed overlaid on the radiation planning fluoroscopic image. In addition, the radiation planning fluoroscopic image with the overlaid radiation area PM is a finalized plan X ray image and is printed onto a sheet by a radiation planning image printing unit 19 or is stored in radiation planning fluoroscopic memory unit 20. The finalized plan X ray image printed by radiation planning image printing unit 19 or stored in radiation planning image memory unit 20 is used as a reference when radiation treatment is actually implemented.

In addition, main control unit 21 has the role of sending commands and data at appropriate times to each of the units of the device depending on input operations from operating unit 17 or the progress of the X ray acquiring and unifies the actions of the device.

Figure 9:
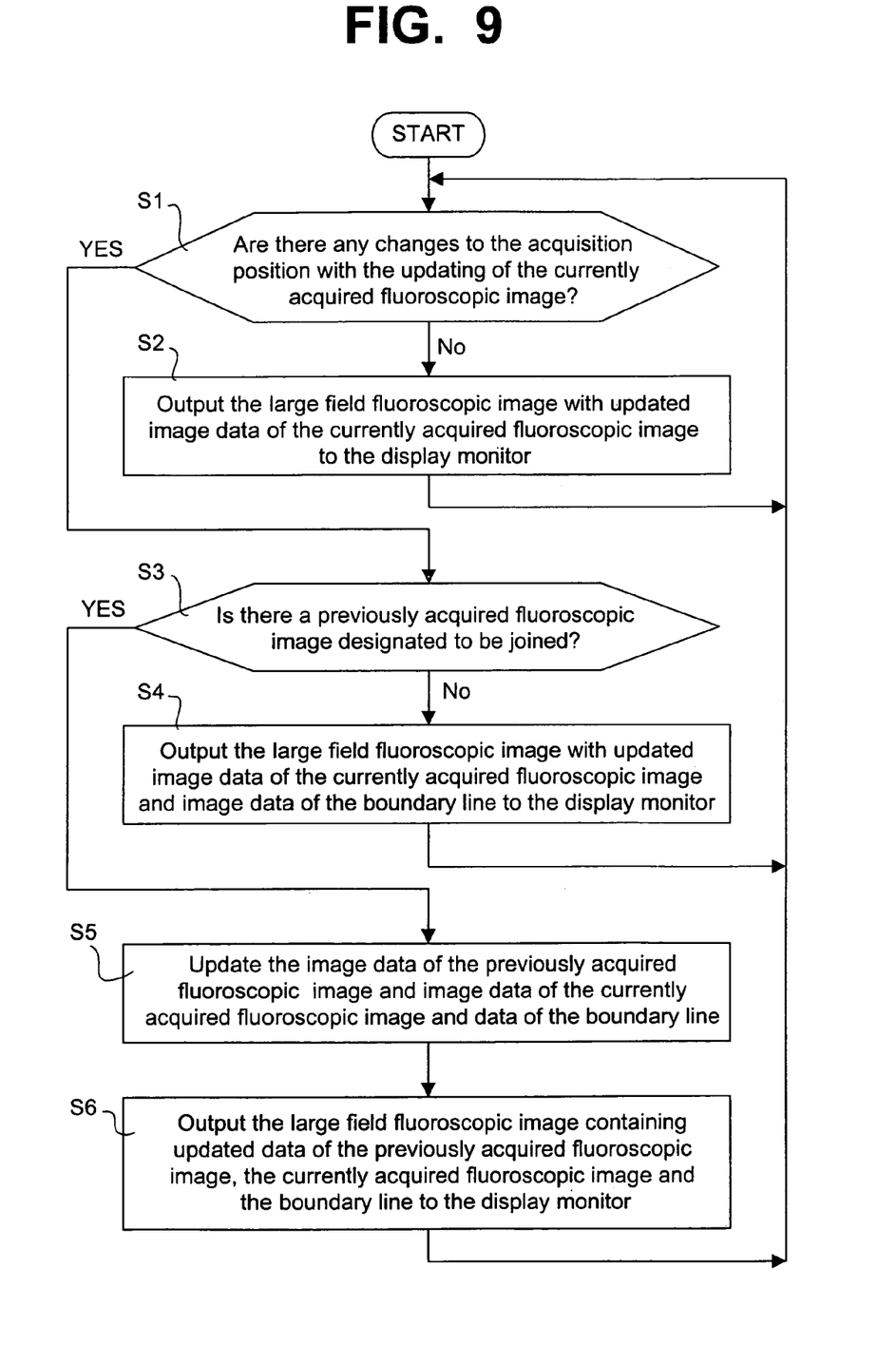
FIG. 9 is a flow chart showing the process for enlarging the field of view of the radiation planning image in the present embodiment.

Next, referring to the drawings, we will describe the capability for enlarging the field of view of the radiation planning fluoroscopic image in the present embodiment having the above constitution. FIG. 9 is a flow chart showing the process for enlarging the field of view of the radiation planning fluoroscopic image in the present embodiment.

A positioning marker (for example a metal chip) is placed on the body surface of subject M, and the subject M is placed on top of table 4. Next, while moving table 4, the positioning marker on the body surface of subject M is matched with the isocenter MC of the embodiment device using a flood light (not shown) provided on the embodiment and which is used for positioning to the standard position. We will next describe the process starting from when fluoroscopic acquiring is initiated. With the start of fluoroscopic acquiring, the planner observes the radiation planning fluoroscopic image on the screen of image display monitor 6. At the same time, the planner can designate the previously acquired fluoroscopic image PB in which expansion of the field of view is needed. In addition, it is assumed that the enlarged fluoroscopic mode has already been selected by operating init 17.

[Step S1] In large field fluoroscopic image data memory unit 13, when the image data of in-progress fluoroscopic image PA is being updated, memory control unit 15 checks whether or not there are any changes in the acquiring position.

If the acquiring position of in-progress fluoroscopic image PA has not been changed, then proceed to next Step S2. If the acquiring position of in-progress fluoroscopic image PA has been changed, then skip to Step S3.

[Step S2] In large field fluoroscopic image data memory unit 13, the image data for in-progress fluoroscopic image PA is updated, and after updating the data, large field fluoroscopic image P as the radiation planning fluoroscopic image is outputted to image display monitor 6. Return to Step 1.

[Step 3] Memory control unit 15 checks whether or not previously acquired fluoroscopic image PB, which is to be pasted to in-progress fluoroscopic image PA, has been designated.

If previously acquired fluoroscopic image PB has not been designated, proceed to Step S4. If previously acquired fluoroscopic image PB has been designated, skip to S5.

[Step S4] In large field fluoroscopic image data memory unit 13, the image data for in-progress fluoroscopic image PA and data for boundary line PL are updated. In addition, after updating the data, large field fluoroscopic image P as the radiation planning fluoroscopic image is outputted to image display monitor 6. Next, return immediately to Step 1.

[Step S5] In large field fluoroscopic image data memory unit 13, image data for previously acquired fluoroscopic image PB is updated. In addition, data for in-progress fluoroscopic image PA and boundary line PL are updated.

[Step S6] In large field fluoroscopic image data memory unit 13, the data for in-progress fluoroscopic image PA, boundary line PL, and previously acquired fluoroscopic image PB have been updated, and large field fluoroscopic image P as the radiation planning fluoroscopic image is outputted to image display monitor 6. Next, return immediately to Step 1.

As long as fluoroscopic acquiring continues and the device continues to be set up for enlarged fluoroscopic mode, the process described in Steps S1–S6 is followed, and large field fluoroscopic image P, in which previously acquired fluoroscopic PB is pasted onto in-progress fluoroscopic image PA, and boundary line PL, which is a boundary indicator showing the boundary between in-progress fluoroscopic image PA and previously acquired fluoroscopic image PB, are shown on the screen of image display monitor 6. This is supplied for observation by the planner.

As described above, with regard to the radiation therapy planning device of the present embodiment, the radiation planning fluoroscopic image shown on the screen of image display monitor 6 is large field fluoroscopic image P in which in-progress fluoroscopic image PA is joined with all or a portion of previously acquired fluoroscopic image PB. In addition, with regard to FPD2, there is no distortion in the image receiving surface, and there are no distortions in the image of large field fluoroscopic image P. As a result, the field of view for radiation planning fluoroscopic image is expanded precisely by the amount of a portion or all of the previously acquired fluoroscopic image PB that is pasted onto in-progress fluoroscopic image PA.

In addition, with boundary line PL which is the boundary indicator that is shown with the radiation planning fluoroscopic image, the area of in-progress fluoroscopic image PA and the area of previously acquired fluoroscopic image PB can be identified at a glance. As a result, even if in-progress fluoroscopic image PA and previously acquired fluoroscopic image PB is displayed simultaneously and contiguous to each other on the screen of the image display monitor, previously acquired fluoroscopic image PB does not interfere in the observation of the radiation planning fluoroscopic image.

Therefore, according to the radiation therapy planning device of the present embodiment, the radiation planning fluoroscopic image, which is for planning the radiation area of subject M for radiation therapy, has a wider field of view.

The present invention is not limited to the above embodiment, and the following changes can be implemented.

(1) In the present embodiment, FPD2 could be moved in the plane of the X ray detection surface. However, this can be modified to a device in which FPD2 cannot be moved in the plane of the X ray detection surface, and the center of the X ray detection surface always coincides with X ray axis XA.

(2) The radiation device used in the radiation therapy planning device of the present invention is not limited to Linac.

According to the radiation therapy planning device of the first implementation, a radiation planning fluoroscopic image shown on a screen of an image display monitor is a large field fluoroscopic image in which an in-progress fluoroscopic image is joined with all or a portion of a previously acquired fluoroscopic image. In addition, with regard to a flat panel X ray detector, there is no distortion in the image receiving surface, and there are no distortions in the image of the large field fluoroscopic image. As a result, the field of view for radiation planning fluoroscopic image is expanded precisely by the amount of a portion or all of the previously acquired fluoroscopic image that is pasted onto in-progress fluoroscopic image.

In addition, by having a boundary indicator displayed together with the radiation planning fluoroscopic image, the area of the in-progress fluoroscopic image and the area of the previously acquired fluoroscopic image can be identified at a glance. As a result, even if the in-progress fluoroscopic image and the previously acquired fluoroscopic image are displayed simultaneously and contiguous to each other on the screen of the image display monitor, the previously acquired fluoroscopic image does not interfere in the observation of the radiation planning fluoroscopic image.

Therefore, according to the radiation therapy planning device of the first implementation, the radiation planning fluoroscopic image, which is for planning the radiation area of a subject for radiation therapy, has a field of view that is suitably wider.

What is claimed is:

1. A radiation therapy planning device, comprising:
   an X-ray tube for irradiating a subject;
   an X-ray detector for detecting fluoroscopic signals of the subject, said detector placed opposite to the X-ray tube.
   an image display monitor for displaying fluoroscopic images for planning a radiation treatment area of the subject,
   wherein said device is configured to display on the monitor all or a part of a fluoroscopic image previously acquired and a fluoroscopic image that is currently being acquired, and said previously acquired fluoroscopic image is disposed over in areas where said current fluoroscopic image corresponds and overlaps with said previously acquired fluoroscopic image; and said device is further configured to display a boundary indicator to demarcate between said currently acquired fluoroscopic image and said previously acquired fluoroscopic image.

2. The radiation therapy planning device according to claim 1, wherein said X ray detector comprises a flat panel X-ray detector.

3. The radiation therapy planning device according to claim 1, further comprising:
   a data collection unit for receiving the fluoroscopic signals from the X-ray detector; and
   a signal processing unit for processing the signals collected by the data collection unit.

4. The radiation therapy planning device according to claim 1, further comprising:
   a field fluoroscopic image data memory unit for storing data of the currently acquired fluoroscopic image and data of non-overlapping areas of the previously acquired fluoroscopic image;
   a previously acquired fluoroscopic image data memory unit; and
   a memory control unit for controlling operations of the field fluoroscopic image data memory unit and the previously acquired fluoroscopic image data memory unit.

5. The radiation therapy planning device according to claim 1, further comprising:
   a bed device disposed between the X-ray tube and the X-ray detector, said bed device configured to move horizontally and vertically.

6. The radiation therapy planning device according to claim 1, wherein the X-ray tube and the X-ray detector are configured to rotate together while maintaining their opposing placement.

7. The radiation therapy planning device according to claim 1, wherein the previously acquired fluoroscopic image and the currently acquired fluoroscopic image form a large field fluoroscopic image in which currently acquired fluoroscopic image is disposed over at the corresponding overlapping areas of the previously acquired fluoroscopic image.

8. The radiation therapy planning device according to claim 1, further comprising:
   a bed device disposed between the X-ray tube and the X-ray detector, said bed device configured to move horizontally and vertically;
   a horizontal transport mechanism device for generating horizontal positional data of the bed device;
   a panel transport mechanism for generating positional data of the X-ray detector,
   wherein the bed device positional data and the X-ray detector positional data are used to determine where the currently acquired fluoroscopic image should be disposed onto the corresponding overlapping areas of the previously acquired fluoroscopic image.

9. The radiation therapy planning device according to claim 8, wherein the device is configured such that if the bed device is moved with respect to the X-ray detector, a position of the currently acquired fluoroscopic image with respect to the previously acquired fluoroscopic image is maintained but a displayed content of the currently acquired fluoroscopic image is changed.

10. The radiation therapy planning device according to claim 8, wherein the device is configured such that if the X-ray detector is moved with respect to the bed device, a position of the currently acquired fluoroscopic image with respect to the previously acquired fluoroscopic image and a displayed content of the currently acquired fluoroscopic image are both changed.

11. The radiation therapy planning device according to claim 8, wherein the device is configured to adjust any image magnification of the previously acquired fluoroscopic image to coincide with a magnification of the currently acquired fluoroscopic image, based on the X-ray device positional data.

12. The radiation therapy planning device according to claim 1, further comprising:
   an operating unit for selecting or deselecting to overlay the currently acquired fluoroscopic image onto the corresponding overlapping areas of the previously acquired fluoroscopic image.

* * * * *